(12) United States Patent
Amshey et al.

(10) Patent No.: US 6,521,111 B1
(45) Date of Patent: Feb. 18, 2003

(54) METHODS AND ARTICLES FOR LABELING POLYMER GELS (75) Inventors: Joseph W. Amshey, Encinitas, CA (US); Allen Bautista, San Diego, CA (US)

(73) Assignee: Invitrogen Corporation, Carlsbad, CA (US)

( * ) Notice: Subject to any disclaimer, the term of this patent is extended or adjusted under 35 U.S.C. 154(b) by 0 days.

(21) Appl. No.: 09/546,574

(22) Filed: Apr. 10, 2000

(51) Int. Cl.[7] .............................. C02F 1/40; C02F 11/00; C25B 11/00; C25B 13/00; C25B 9/00; G01N 27/27; G01N 27/403; G01N 27/453
(52) U.S. Cl. ........................................ 204/616; 204/600
(58) Field of Search ...................................... 204/1, 600

(56) References Cited

U.S. PATENT DOCUMENTS

| | | | |
|---|---|---|---|
| 3,549,406 A | 12/1970 | Ambusk | 117/34 |
| 3,960,499 A | 6/1976 | White | 23/253 |
| 4,072,639 A | 2/1978 | Yamaguchi et al. | 260/6 |
| 4,094,759 A * | 6/1978 | Ruhenstroth-Bauer et al. | 204/466 |
| 4,415,428 A | 11/1983 | Nochumson et al. | 204/299 |
| 4,569,794 A | 2/1986 | Smith et al. | 260/6 |
| 4,600,641 A | 7/1986 | Ogawa et al. | 428/355 |
| 4,717,667 A * | 1/1988 | Provonchee | 435/30 |
| 4,718,998 A | 1/1988 | Ogawa et al. | 204/299 |
| 4,737,259 A | 4/1988 | Ogawa et al. | 204/299 |
| 4,915,811 A | 4/1990 | Yamamoto et al. | |
| 4,929,972 A | 5/1990 | Anderson et al. | |
| 5,055,517 A | 10/1991 | Shorr et al. | 524/813 |
| 5,128,412 A | 7/1992 | Miyasaka et al. | 525/108 |
| 5,212,299 A * | 5/1993 | Smith | 106/205.9 |
| 5,219,923 A | 6/1993 | Shorr | 524/827 |
| 5,238,651 A | 8/1993 | Chuba | |
| 5,306,468 A | 4/1994 | Anderson et al. | |
| 5,397,449 A | 3/1995 | Zewert et al. | 204/182.8 |
| 5,455,344 A * | 10/1995 | Harper et al. | 536/123.1 |
| 5,476,016 A | 12/1995 | Fedorka-Cray et al. | |
| 5,641,626 A * | 6/1997 | Dumais et al. | 435/6 |
| 5,670,226 A | 9/1997 | Yoshizawa et al. | 428/40.1 |
| 5,672,416 A | 9/1997 | Radola et al. | 428/247 |
| 5,681,437 A | 10/1997 | Black et al. | |
| 5,885,432 A | 3/1999 | Hooper et al. | 204/469 |
| 5,954,931 A * | 9/1999 | Maracas et al. | 204/451 |
| 5,990,238 A | 11/1999 | DiZio et al. | 525/60 |
| 5,993,627 A * | 11/1999 | Anderson et al. | 204/456 |
| 6,017,624 A | 1/2000 | Delgado et al. | 428/355 |
| 6,090,255 A | 7/2000 | Riley et al. | |
| 6,123,821 A * | 9/2000 | Anderson et al. | 204/456 |
| 6,136,173 A * | 10/2000 | Anderson et al. | 204/461 |
| 6,139,709 A * | 10/2000 | Scott | 204/615 |
| 6,187,250 B1 * | 2/2001 | Champagne | 204/470 |
| 6,245,206 B1 * | 6/2001 | Anderson et al. | 204/461 |
| 6,251,516 B1 * | 6/2001 | Bonner et al. | 428/346 |
| 6,277,630 B1 * | 8/2001 | Brophy et al. | 422/102 |
| 6,278,794 B1 * | 8/2001 | Parekh et al. | 382/129 |

FOREIGN PATENT DOCUMENTS

| | | | |
|---|---|---|---|
| DE | 3032069 | 6/1982 | C09D/5/40 |
| DE | 3032071 | 7/1982 | G01N/1/28 |
| DE | 3032070 | 10/1982 | B01D/57/02 |
| JP | 09111198 A * | 4/1997 | C09J/7/02 |

OTHER PUBLICATIONS http://www.dupont.com/industrial–polymers/nucrel/.*
"GelBond® film", downloaded from http://www.bmaproducts.com/product . . . , 6 pages, Mar. 27, 2000.
"GelBond® PAG film", downloaded from http://www.bio-products.com/product . . . , 4 pages, Mar. 27, 2000.

* cited by examiner

Primary Examiner—Lyle A. Alexander
Assistant Examiner—Jennine Brown
(74) Attorney, Agent, or Firm—Fish & Neave; Edward J. DeFranco; Daniel M. Becker (57) ABSTRACT

The invention provides methods, apparatus and kits for integrally labeling polymeric gels, such as polyacrylamide and agarose gels, with indicia that can serve, inter alia, unambiguously to identify the individual gel, using polymeric film labeled with detectable indicia and coated with materials that bond to the gel matrix as the gel polymerizes.

46 Claims, 7 Drawing Sheets

METHODS AND ARTICLES FOR LABELING POLYMER GELS

FIELD OF THE INVENTION

The present invention relates to gel electrophoresis. More particularly, this invention relates to methods, articles and kits for labeling polymer gels used for gel electrophoresis.

BACKGROUND OF THE INVENTION

Gel electrophoresis is among the most common analytical procedures used in biologic research, and is used to characterize, separate, and at times to purify a wide variety of biological molecules, including deoxyribonucleic acid ("DNA"), ribonucleic acid ("RNA") and proteins.

The basic principles are well established. A gel, such as polyacrylamide or agarose, is first solidified from a liquid solution by polymerization within a rigid gel casting form. To effect separation of an analytical mixture, an electric potential is applied across the length of the polymer gel, either as enclosed within the casting form or, particularly in the case of agarose gels, after removal of the gel from the casting form. Charged analytes placed within the gel are then separated and distinguished from one another based upon their differential mobility through the gel matrix under the motivating influence of the applied electric field.

Researchers either prepare their own gels or purchase them precast from commercial suppliers. Frequently, large numbers of gels are prepared and run. Where such gels are of identical dimension, it is critical that the gels be distinguished from one another so that results of various experiments are not confused with one another and the results misinterpreted.

However, it is difficult to mark the gel surface (e.g., by writing on the gel), and the gel shape may not easily be modified without disturbing the uniformity of the electric field desired to be maintained in the gel during electrophoresis. Although the gel cassette in which the electrophoresis may have been conducted can readily be labeled, such a label does not remain with the gel once the gel is removed for staining or further processing.

Furthermore, it is frequently difficult after electrophoresis to determine the orientation that the gel had maintained during electrophoresis. For example, the researcher may be unable readily to determine after electrophoresis which side of the gel had been proximal to the anode and which proximal to the cathode, particularly if the sample wells have been removed from the gel.

One known technique for labeling and orienting polymer gels is to remove the gel from its enclosing cassette after performing electrophoresis, and then notch or cut one of the gel's four corners. This technique, however, does not provide an identification mark that is visible both prior to and following electrophoresis. Nor does this technique provide unambiguous identification, especially when several gels are being stained or processed simultaneously. And because the gels have at most four corners that may be notched, this technique allows at most four gels to be identified at a time.

Another previously known technique for labeling gels is to include within the gel a piece of filter paper that contains identifying marks, such as written or printed characters. This technique, however, causes both physical and optical problems.

The filter paper can, for example, cause localized disturbance in the electric field, either directly, or indirectly through a local change in temperature or electrolyte concentration, thus distorting the migration of analytes through gel. The paper, although physically entrapped in the gel, may still separate therefrom, or may weaken the gel so that the gel breaks easily, allowing the label to come free.

The filter's opacity may obscure detection of analyte in portions of the gel that it overlies. Furthermore, following electrophoresis, the filter paper may take up the stains that are used to render the analytes themselves detectable, further obscuring the analytes in the gel. It goes without saying that the filter is unsightly.

Transparent films have been described that are useful for imparting structural rigidity to polymer gels used in gel electrophoresis. The films, when placed in contact with the gel during polymerization, bond irreversibly to the polymerized gel, either by covalent or strong noncovalent bonds. These films, available commercially, have not been taught to be useful if smaller in surface area than the gel to be supported thereon. Such films have also not been taught to be useful substrates for applying indicia that would serve unambiguously to identify the adherent gel.

It would be desirable to provide improved methods, articles and kits for labeling polymer gels used for gel electrophoresis.

It would further be desirable to provide methods, articles and kits for labeling gels whereby the label does not interfere with electrophoresis or with post-electrophoresis processing and does not easily separate from the gel.

It would also be desirable to provide methods, articles and kits for labeling polymer gels used for gel electrophoresis whereby the label has an aesthetically pleasing appearance and where the label's substrate is, preferably, substantially transparent.

SUMMARY OF THE INVENTION

These and other objects are solved by the present invention, which provides novel methods, articles, and kits for labeling polymer gels used for gel electrophoresis.

In a first aspect, the invention provides methods for detectably labeling a polymer gel, comprising bonding a polymeric film to the gel during gel polymerization. The polymeric film has indicia that are detectable after the film is so bonded, thereby permanently labeling the gel.

In another aspect, the invention provides labeling articles for use in the aforesaid methods. The article comprises a polymeric film having detectable indicia, and, optionally, a coating. When the coating is absent, the polymeric film is itself capable of bonding to the polymeric gel during its polymerization. When the coating is present, the coating is capable of bonding the polymeric film to the gel during polymerization. In either case, the indicia are detectable after the film is so bonded.

The methods and articles of the present invention are useful with polymer gels of a wide variety of compositions, including polyacrylamide, agarose, and derivatives thereof.

In a typical embodiment, the polymeric film is a polyester with a single layer coating of hydrophilic resin with ethylenically unsaturated groups, or a polyester film with a two-layer coating wherein the first layer is a vinyl acetate-maleic acid copolymer in direct contact with the film, and the second layer is a layer of dried agarose.

Often, the indicia will be detectable both before and after electrophoresis, either by epiillumination, transillumination, or both. In some embodiments, the indicia will be detectable using natural light for illumination; in other embodiments, the indicia are detectable only after illumination with non-visible wavelengths.

In another aspect, the invention provides pre-cast polymer gels labeled with detectable indicia, comprising: a polymer gel; and a polymeric film having detectable indicia, wherein the polymeric film is bonded to the polymer gel and the indicia are detectable with the film so bonded.

The invention further provides a kit for labeling a polymer gel, comprising: at least one labeling article packaged in association with instructions for bonding the label to a polymer gel during gel polymerization.

BRIEF DESCRIPTION OF THE DRAWINGS

The above-mentioned objects and features of the present invention can be more clearly understood from the following detailed description considered in conjunction with the following drawings, in which like reference numerals denote like structural elements throughout, and in which.

DETAILED DESCRIPTION OF THE INVENTION

Applicants have invented methods, articles of manufacture, and kits for labeling polymer gels based upon the use of clear polymeric films bearing detectable indicia. The polymeric film, when contacted to the gel during its polymerization, bonds irreversibly, rendering the identifying indicia integral to the gel itself. The indicia are detectable after the film is so bonded to the gel.

Methods of preparing, casting, and performing electrophoresis using polymer gels are well known, and need not be detailed here. See, e.g., Westermeier, *Electrophoresis in Practice*, 2nd ed. (John Wiley & Sons, 2000) (ISBN 3527300708); *Gel Electrophoresis of Proteins*, B. D. Hames et al. (eds.), 3rd edition (Oxford University Press, November 1998) (ISBN 0199636419); and Jones, *Gel Electrophoresis: Nucleic Acids: Essential Techniques*, (John Wiley & Son Ltd. 1996) (ISBN 0471960438), the disclosures of which are incorporated herein by reference in their entireties.

Although polyacrylamide (that is, a polymerization product of acrylamide monomer crosslinked with N,N'-methylenebisacrylamide) and agarose are the two polymeric gels most commonly used in electrophoresis today, and will therefore be used to exemplify the invention herein, the present invention proves useful in labeling a far wider variety of polymeric gels, including, for example: polymers formed by polymerization of acrylamide monomers, such as N-methylolacrylamide, with cross-linking agents or co-monomer agents such as tetraethylene diacrylate and bisacrylamide methylether, as described in Shorr, U.S. Pat. No. 5,219,923; polymers formed by cross-linking polymerization of N,N-dimethylacrylamide with ethyleneglycol methacrylate and polymers formed by cross-linking polymerization of N,N-dimethylacrylamide and hydroxyethylmethacrylate with N,N-dimethylbisacrylamide, as described in Shorr et al., U.S. Pat. No. 5,055,517; polymers formed by crosslinking polymerizing or copolymerizing if hydroxy alkyl esters of acrylic or methylacrylic acid or poly(alkylene glycol) esters of acrylic or methacrylic, as described in Zewert et al., U.S. Pat. No. 5,397,449; un-crosslinked polymers which have a temperature reversible transition from low viscosity to high viscosity, so as to be pourable at one temperature, while providing sieving properties at another temperature, as described in Hooper et al., U.S. Pat. No. 5,885,432; and modified (i.e., nonnatural) agaroses, such as low melting point agaroses and NuSieve® agarose (FMC BioProducts, Rockport, Me.). The only physical limitation on the type of polymer gel that can be labeled is that it be capable of bonding to the polymeric film of the label, as will now be described.

Figure 3:
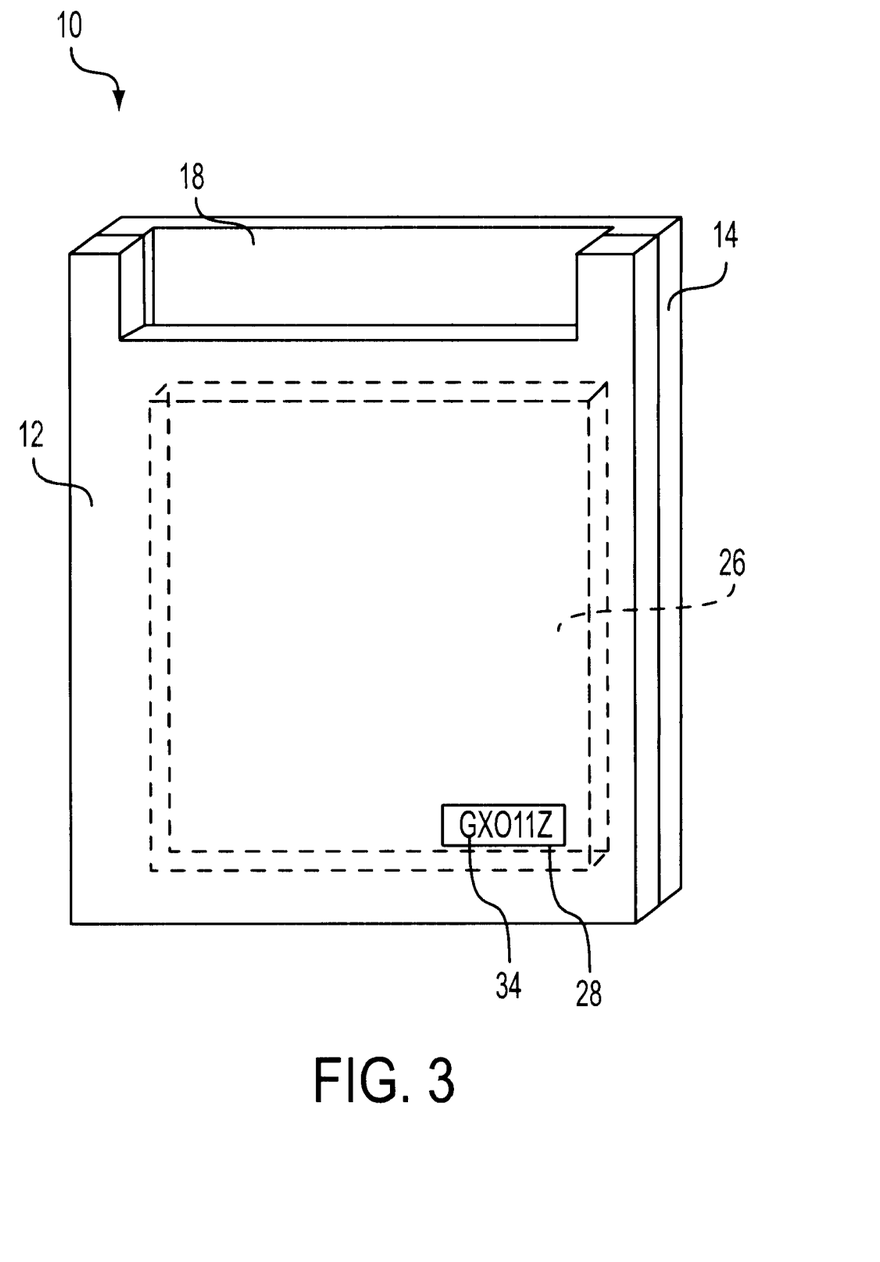
FIG. 3 is a schematic diagram of a gel cassette and gel that further includes a gel label in accordance with this invention.
Figure 4:
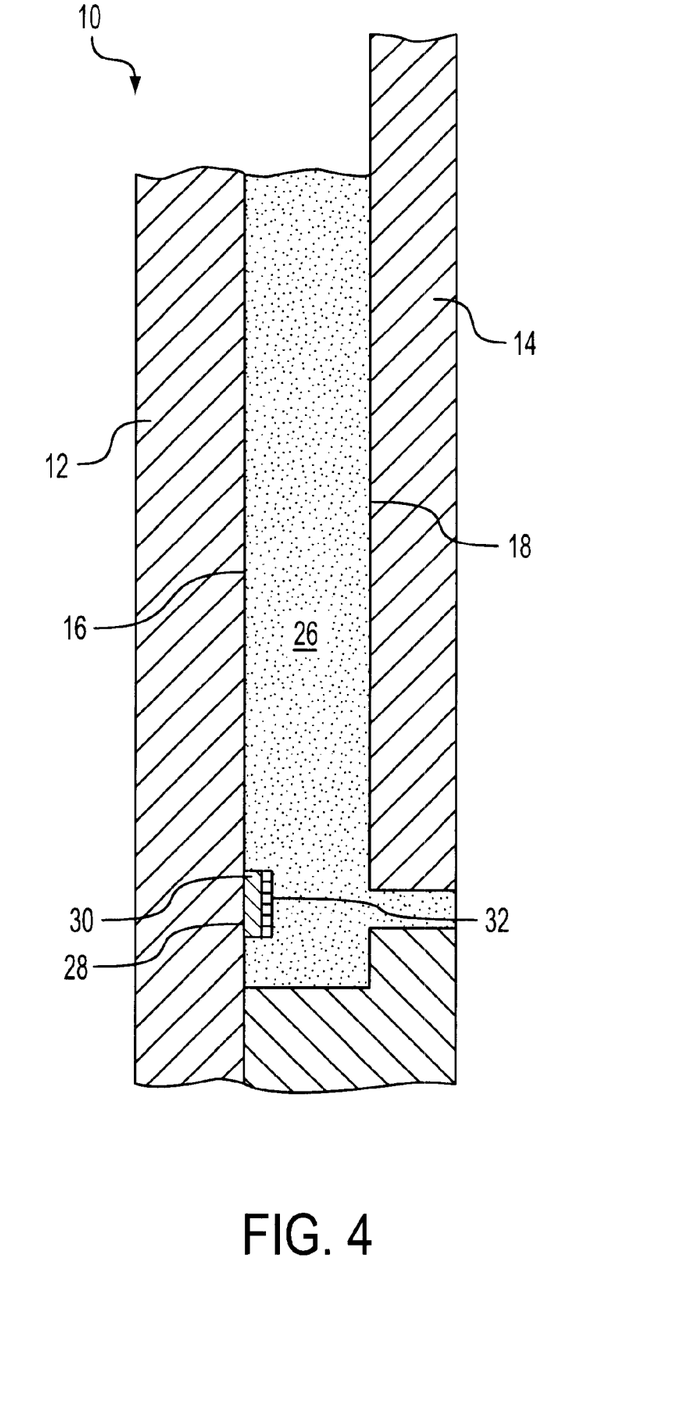
FIG. 4 is a partial cross-sectional view of the gel cassette, gel and gel label of FIG. 3.

Gel label 28 comprises polymeric film 30, optionally but typically coating 32 and, optionally but typically, indicia 34.

Polymeric film 30 provides shape and structural rigidity to gel label 28. Although polymeric film 30 can be completely rigid, it typically takes the form of a flexible film. Accordingly, gel label 28 can be provided in the form of rolls as well as in individual sheets, as further described below.

Typically, polymeric film 30 is no more than about 1 mm thick, typically no more than about 0.5 mm thick, more typically no more than about 0.25 mm thick, and most typically no more than about 0.2 mm thick. Polymeric film 30 can be as little as 0.01 mm thick, and more typically is at least about 0.05 mm thick, most typically at least about 0.1 mm thick.

When gel 26 is prepared by chemical cross-linking of monomers, polymeric film 30 should be capable of contact with gel components during the polymerization process without suffering significant deterioration of desired structural or optical properties. When gel 26 is prepared by cooling of a molten liquid, as is typical in preparing agarose gels for electrophoresis, polymeric film 30 should be capable of contact with such molten liquid without suffering significant deterioration of desired structural or optical properties.

With respect to structural properties of polymeric film 30, it will typically be desired that polymeric film 30 not suffer significant deformation during polymerization/solidification of the gel, so as not to assume a three dimensional conformation that would induce localized disturbance in the electric field within the gel. Furthermore, where gel label 28 includes a ruler within indicia 34 (see below), it will typically be desired that polymeric film 30 not be significantly altered in shape or size by contact with the gel during the polymerization/solidification, so as to preserve the reliability of the measured markings included thereupon.

With respect to the optical properties of polymeric film 30, it will typically be desired that polymeric film 30 be transparent, although translucent or opaque films can also be used. Transparency of polymeric film 30 creates the least impediment to the detection of analytes present within the gel, particularly where transillumination is required for visualization. When desired to be transparent, polymeric film 30 should not be significantly opacified by contact with the gel during polymerization or solidification.

Polymeric film 30 can usefully be composed of polyester, mylar, polymethylpentene (manufactured by Mitsui & Co., Ltd., Japan), polystyrene, polypropylene, polyethylene, styreneacrylonitrile copolymers, polycarbonate, cellulose acetate proprionate, cellulose acetate butyrate, nitrile-acrylonitrilestyrene copolymers, polyacrylate, polyterephthalate, polymethacrylate, acrylonitrile-butadiene-styrene copolymers, or other similar polymeric films known in the art.

Polymeric film 30 is typically treated to render its surfaces more hydrophilic. Increased hydrophilicity can aid in the subsequent bonding of coating 32, where coating 32 is a hydrophilic resin. Increased hydrophilicity can also facilitate the direct bonding of hydrophilic polymeric gels, particularly agarose gels, to polymeric film 30. Where gel label 28 is to be used with agarose gels, surface treatment of polymeric film 30 to render it hydrophilic can alone suffice, without addition of coating 32, to provide adhesion of label 28 to gel 26 that is sufficient to label the gel in accordance with the methods of the present invention. In the more usual case, however, coating 32 will nonetheless additionally be applied to polymeric film 30 in the manufacture of gel label 28.

Surface treatment of polymeric film 30 can be accomplished using any well-known technique for introducing surface-accessible polar groups into the hydrophobic polymeric backbone, such as plasma arc processing, as described in Ambusk, U.S. Pat. No. 3,549,406, concentrated sulfuric acid processing, as described in White, U.S. Pat. No. 3,960,499, and epoxy compound processing, as described in Yamaguchi et al., U.S. Pat. No. 4,072,639, the disclosure of each of which is incorporated herein by reference in its entirety. Surface treatment techniques that are particularly useful in the practice of the present invention are described in Nochumson et al., U.S. Pat. No. 4,415,428, the disclosure of which is incorporated herein by reference in its entirety.

Polymeric film 30 can be a unilaminate sheet, or alternatively can be provided as a multilaminate structure, so long as the laminate as a whole retains the physical and optical properties desired of polymeric film 30.

In another embodiment, polymeric film 30 is a polycarbonate film perforated with a uniform density of etched holes, available in a variety of pore sizes from Whatman, Inc. (Clifton, N.J.) under the brand name Nucleopore®. In this embodiment, adherence of polymeric film 30 to polymer gel 26 is effected by permeation of the holes during gel polymerization, gel crosslinking serving to secure the gel to the film. Addition of an optional vinyl-containing coating 32 could further facilitate bonding of polyacrylamide gels to such film, as will now more particularly be described.

Coating 32, which is bonded to polymeric film 30, serves to bond polymeric film 30 to gel 26. As noted above, coating 32 need not be included in gel label 28 when surface hydrophilicity of polymeric film 30 suffices to effect adequate bonding of polymeric film 30 directly to gel 26. In the more typical case, however, coating 32 will be used to ensure that bonding to gel 26 of gel label 28 is adequate to ensure permanent labeling of the gel.

The composition of coating 32 will be dictated in part by the composition of the gel to be labeled in accordance with the present invention, although certain coatings 32 will prove useful for adhering polymeric film 30 to gels of several compositions.

For polyacrylamide gels, coating 32 can usefully be a material that will covalently link to gel 26 during its polymerization. Particularly useful are hydrophilic resins that contain reactive ethylenically unsaturated groups, such as allylglycidylagarose and allylglycidyldextran, the preparation and composition of which are described in Nochumson et al., U.S. Pat. No. 4,415,428 ("Nochumson"), the disclosure of which is incorporated herein by reference in its entirety. These derivatized polyols prove useful additionally for bonding polymeric film 30 to agarose gels, which adhere to the hydrophilic resin by presumed noncovalent physical forces, such as hydrogen bonding and van der Waal's interactions.

Also useful as coating 32, particularly for noncovalent attachment of polymeric film 30 to agarose gels, are those coatings described in Grubhofer, DE 3,032,071 (see also Grubhofer, DE 3,032,069 and DE 3,032,070) (collectively, "Grubhofer"), in which a coating of vinyl acetate-maleic acid copolymer is first adhered to a polyester film, then further coated with a thin layer of agarose and dried.

Coating 32 can be applied to polymeric film 30 by any of a variety of appropriate means that would be well known in the art. Most conveniently, coating 32 can be applied in liquid form and the coated film then dried. Where polymeric film 30 is provided in rolls, such wetting and drying can be done on a continuous basis by using continuous pass-through baths and ovens.

For example, polymeric film 30, after surface treatment with oxygen plasma, can be contacted briefly with an aqueous solution of allylglycidyl agarose, then dried in an oven at 100° C. for 20 minutes, as described in Nochumson. Nochumson also describes coating polymeric film 30 directly, without antecedent surface treatment, by contacting the film with a 0.5% solution of allylglycidyl agarose in 0.1% Triton X-100, the detergent facilitating adequate bonding of coating 32 to polymeric film 30.

Similarly, Grubhofer reacts maleic acid anhydride with various unsaturated compounds such as hexadecene-1, allyl alcohol, vinylmethylether and vinylamine. The coating is applied by drawing the film through an acetone solution of the copolymer and drying with heat.

Coating 32, as suggested above, can consist of a unitary layer of uniform composition, but can also consist of multiple layers, each having a unique composition.

Polymeric film 30 having coating 32 and adequate to function as gel label 28 upon addition of indicia 34, can be purchased commercially.

Examples of commercially-available products that can be used to provide gel labels in accordance with this invention include GEL-FIX® film, manufactured by Invitrogen, Inc. (Carlsbad, Calif.), a clear polyester film prepared according to the methods of Grubhofer, GelBond® film (FMC Bioproducts, Rockland, Me.), particularly adapted to bonding to agarose gels, and GelBond®-PAG, particularly adapted to bond covalently to polyacrylamide gels during gel polymerization.

As shown in FIG. 3, gel label 28 can, but need not necessarily, include indicia 34 which are useful in identifying gel 26. Gel label 28 need not include such indicia when the size and/or shape of the label is itself diagnostic of the identity of the gel to which the gel label is bonded.

Indicia 34 can be one or more alphanumeric characters, bar codes, or similar symbols that provide an identification of individual gels.

Indicia 34 can be composed of any substance that will be detectable when identification of gel 26 is desired to be effected. The indicia can be composed of substances that are detectable upon either epiillumination (that is, illumination from the side of the gel being viewed), upon transillumination (that is, illumination through the gel from the side opposite that being viewed), or upon both.

If identification is desired prior to electrophoresis and staining, indicia 34 will be composed of a substance that is detectable prior to electrophoresis and staining, and typically without further processing of the gel.

For example, for detectability under normal lighting conditions, indicia 34 can be composed of one or more visible inks, including, e.g., India ink. The ink can be applied to polymeric film 30 by any of a number of means, the choice of which will be dictated in part by whether gel label 28 is to be provided to the electrophoresis end user with indicia 34 already present thereon, or instead is to be provided to the user without indicia 34, which are thereafter to be applied.

In the former case, any printing technique compatible with polymeric film 30 can be used. A printing technique is said to be compatible with polymeric film 30 if use thereof does not adversely affect the usability of polymeric film 30 in the practice of the present invention, as, e.g., by causing it to become unusably opaque. Thus, indicia 34 can be applied by typewriter, ink-jet printer, by laser printer, or the like.

In the latter case, in which gel label 28 is provided to the electrophoresis user without indicia 34, indicia 34 can thereafter be applied by the user by etching or scribing into the surface of polymeric film 30 by pen.

Indicia 34 can also be created by selectively opacifying portions of polymeric film 30, or of a dye layer applied thereto. If polymeric film 30 is a multilaminate structure, such dye layer can be present internal to such laminate. Selectively opacifiable dyes are well known in the recordable optical media arts, and include various types of cyanine and phthalocyanine dyes. Where such dyes are present, indicia 34 can be applied by directing a laser of appropriate wavelength thereupon to form symbols or characters in the film by heating the photosensitive compound until it becomes opaque (or absorptive).

Indicia 34 can alternatively, or additionally, be composed of substances that are detectable only with specialized lighting. Indicia 34 can include, for example, one or more fluorescent dyes that are visible only, or predominantly, when epi- or transilluminated at the excitation wavelength of the fluorophore.

Such fluorescent dyes can be chosen for excitation and emission spectra compatible with standard laboratory equipment, such as ultraviolet transilluminators, and thus to have excitation and emission spectra similar to those of fluorescent dyes typically used in nucleic acid and protein analysis. Alternatively, the dye can be chosen to have excitation and/or emission spectra sufficiently distinguishable from those of dyes used in protein and/or nucleic acid analysis that indicia 34 will be readily distinguished therefrom. A wide selection of fluorescent dyes suitable for these purposes are described in Haugland, *Handbook of Fluorescent Probes and Research Chemicals*, 7$^{th}$ ed. (Molecular Probes, Inc., Eugene, Oreg.), incorporated herein by reference in its entirety.

If identification of gel 26 is desired to be effected after electrophoresis and/or staining, indicia 34 can additionally be composed of any substance that becomes, or can be made to become, detectable after electrophoresis and/or staining.

For example, where the analytes to be separated on the gel are proteins, indicia 34 can be composed of substances that become detectable after the gel is stained with protein-visualizing dyes, such as Novex® Colloidal Blue Staining Kit (Invitrogen, Inc., Carlsbad, Calif.), SERVA® Blue R (Invitrogen, Inc., Carlsbad, Calif.) or other brand of Coomassie™ R-250 stain, SERVA® Blue W (Invitrogen, Inc., Carlsbad, Calif.), SERVA® Blue G (Invitrogen, Inc., Carlsbad, Calif.), SERVA® Violet 17 (Invitrogen, Inc., Carlsbad, Calif.), and silver stain. The substances will typically be those that resist the subsequent gel destaining steps.

Where the analytes to be separated on the gel are nucleic acids, indicia 34 can be composed of substances that become detectable after the gel is stained with dyes used for visualizing nucleic acids, such as ethidium bromide or SYBR® Green (Molecular Probes, Inc., Eugene Oreg.; Invitrogen Inc., Carlsbad, Calif.).

Alternatively, or in addition, indicia 34 can be composed of substances that are rendered visible by the electrophoresis process itself, either through contact with molecules that are present in the running buffer, such as electrolytes, or through the application of the electric field itself. The latter can be accomplished through use of liquid crystal display elements in indicia 34.

An advantage of fabricating indicia 34 from one or more substances that become detectable after electrophoresis and/or staining is that such indicia can additionally serve as a positive control for the electrophoretic and/or staining process.

Indicia 34 can also be composed of substances that can be rendered detectable by a staining process distinct from that required to render the separated analyte detectable.

Indicia 34 can, for example, include substances that are detectable by subsequent contact with a labeled reagent specific therefor, such as an antibody. The antibody can be labeled directly or indirectly by any of the means well known in the biologic arts, including conjugation to an enzyme, conjugation to a fluorophore, or conjugation to a chemiluminescent compound. By indirect labeling is intended the binding to the primary detection agent of a secondary agent that is itself labeled, such as a secondary antibody.

Where the detection reagent is conjugated to an enzyme, the enzyme substrate will determine whether indicia 34 are detectable under normal illumination or require specialized illumination and/or detection. For example, if the enzyme is alkaline phosphatase, a BCIP/NBT substrate will result in localized deposition of a precipitate visible in natural light, whereas use of a CDP-Star® chemiluminescent substrate (available from Invitrogen, Inc., Carlsbad, Calif.), results in photonic emission detectable on film, CCD, PhosphorImager® (Molecular Dynamics, Inc., Sunnyvale, Calif.), Storm® Imager (Molecular Dynamics, Inc., Sunnyvale, Calif.), or Typhoon® Imager (Molecular Dynamics, Inc., Sunnyvale, Calif.).

As another example, indicia 34 can include peptides having multiple histidine residues capable of forming complexes with heavy metal chelates such as nickel nitrilotriacetic acid. See, e.g., U.S. Pat. No. 4,569,794, incorporated herein by reference in its entirety. Commercially available reagents that permit such peptide/nickel-NTA chelates specifically to be detected are well known in the art. If the analyte to be detected after electrophoresis on the gel is to be detected by nickel-NTA chelate chemistry—for example, if the analyte is a recombinantly expressed fusion protein with poly-histidine tag—detection of the analyte and indicia 34 can be effected simultaneously.

As mentioned above, indicia 34 can be used in the methods of the present invention uniquely to identify the polymeric electrophoresis gel. If applied by the gel user, indicia 34 can include, for example, a date of experiment, an arbitrary or sequential reference number, a sample identifier, or the like.

Gel label 28 can also be provided to the user with indicia 34 already present thereon. Such indicia can include, e.g., sequential numbers, permitting the rapid and unique labeling of a series of gels. Such gel labels can also include an area for user application of a further identifier.

Gel label 28 can also be provided as part of a pre-cast gel 26. In such case, indicia 34 of gel label 28 can usefully provide information on the gel composition, pore size, buffer composition, original gel pH, date of manufacture, recommended date of expiration, manufacturer name, catalogue number, and the like. Where the pre-cast gel is used for isoelectric focusing, such as a Servalyt Precotes® gel (Invitrogen, Carlsbad, Calif.), indicia 34 of gel label 28 can include information on the gel's pH range.

Where gel label 29 is provided as part of a pre-cast gel 26, indicia 34 can also usefully include a preprinted marker of gel orientation, particularly useful for two-dimensional electrophoretic applications, and can additionally include markings that highlight the location and extent of sample loading wells, thus facilitating sample addition. Pre-cast gels for a variety of electrophoretic uses are available commercially from Invitrogen, Inc. (Carlsbad, Calif.), Amersham Pharmacia Biotech (Piscataway, N.J.), Stratagene (La Jolla, Calif.), Amresco Inc. (Solon, Ohio), Bio-Rad Laboratories (Richmond, Calif.) and others.

The substances from which indicia 34 are made can also comprise molecules that report the contemporaneous physical state of the gel. Particularly useful in this regard are pH indicators and temperature indicators. Both categories of indicators are well known in the analytical arts.

Depending on the shape of gel label 28, a detectable ruler can usefully be included among indicia 34.

Rulers are used in the electrophoretic art to provide a direct measure of analyte migration distance. Such rulers are typically extrinsic to the gel, and the distances traveled are memorialized by photographing the ruler placed alongside the gel prior to any drying of the gel. Where the analyte is detected using ultraviolet transillumination—for example, UV transillumination of ethidium-bromide or SYBR® green-stained nucleic acids—the extrinsic ruler is adapted to fluoresce. A disadvantage of such extrinsic rulers is a requirement for such memorialization, and the difficulty after staining of exactly aligning the ruler to the gel. If gel label 28 extends from sample well sufficiently far toward the opposite end of the gel, a ruler can be made intrinsic to the gel by constituting part of indicia 34.

Figure 5:
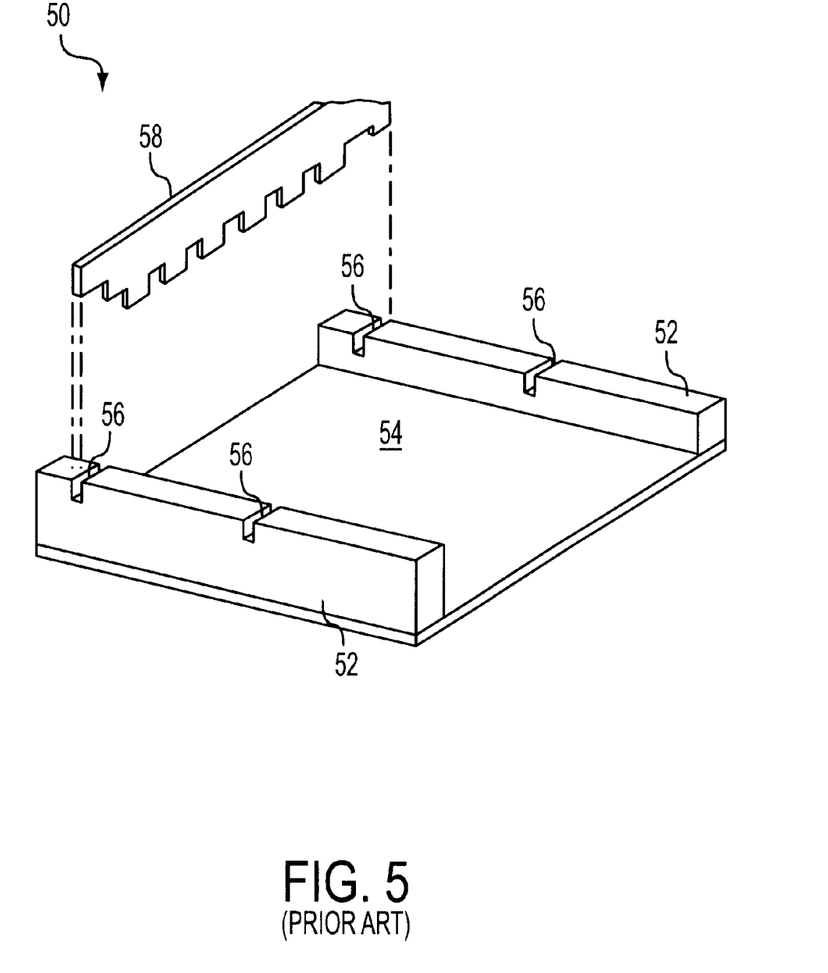
FIG. 5 is a top perspective view of a prior art casting form used for casting agarose gels suitable for submerged horizontal slab gel electrophoresis.

Gel label 28 can be manufactured in any shape or size that is compatible with electrophoresis of the gel to which it is to be bonded. Typically, therefore, it will be no larger than plate 14, where electrophoresis is accomplished between spaced plates, or, in the case where the gel is run as a horizontal slab without an enclosing top plate (e.g., an agarose slab gel), no larger than casting tray 50 (see below) upon which the gel is to be run. Conversely, gel label 28 can be as small as will readily be detectable after electrophoresis and, typically, no smaller than can conveniently be handled.

When as large or larger than gel 26 itself, gel label 28 serves to provide structural rigidity and support to the gel through electrophoresis and staining, and will provide a permanent backing if the gel is subsequently dried.

When gel label 28 is intended to be as large or larger than gel 26, it can conveniently be provided in sheets with dimensions substantially identical to those of commercial cassettes and casting trays, respectively, such as the Xcell SureLock™ mini-cell (Invitrogen, Carlsbad, Calif.).

As mentioned above, gel label 28 can alternatively be provided prior-bonded to a pre-cast gel. In such case, gel label 28 can conveniently be as large as the gel itself, providing structural support to the gel.

Alternatively, gel labels 28 can be provided in sheets or rolls that can be cut to chosen dimension. Alternatively, gel labels 28 can be provided in sheets or rolls having perforations to facilitate the removal from the sheet or roll of labels of desired size.

Particularly useful are gel labels 28 that include, on a surface other than that intended to contact gel 26, an impermanent pressure-sensitive adhesive, such as is described in U.S. Pat. Nos. 6,017,624; 5,990,238; 5,128,412; and 5,670,226, the disclosures of which are incorporated herein by reference in their entireties. Such labels can be provided with a backing sheet, thereafter to be peeled off the backing sheet and placed in the electrophoresis apparatus. Alternatively, the adhesive can be bonded to the backing sheet rather than to the gel labels.

As mentioned above, the shape of gel label 28 can itself provide indicia of gel identity. Such unique shapes can readily be cut from a coated polymeric film 30 by the user. Alternatively, gel labels 28 can be provided to the user in a plurality of discrete shapes. In addition to varying shape, varying numbers of gel labels can be applied to the gel to provide an indicium of identity.

To label a gel according to the methods of the present invention, gel label 28 is placed in contact with the gel matrix prior to or concomitant with polymerization thereof. Where gel label 28 includes coating 32, the label is placed so that coating 32 contacts the gel. How such contact is effected depends upon the electrophoresis format.

The gel labeling methods, labels, and kits of the present invention are particularly useful for two electrophoresis formats: vertical slab gels and horizontal slab gels, although they may find use additionally in tube and capillary gel electrophoresis.

Figure 1:
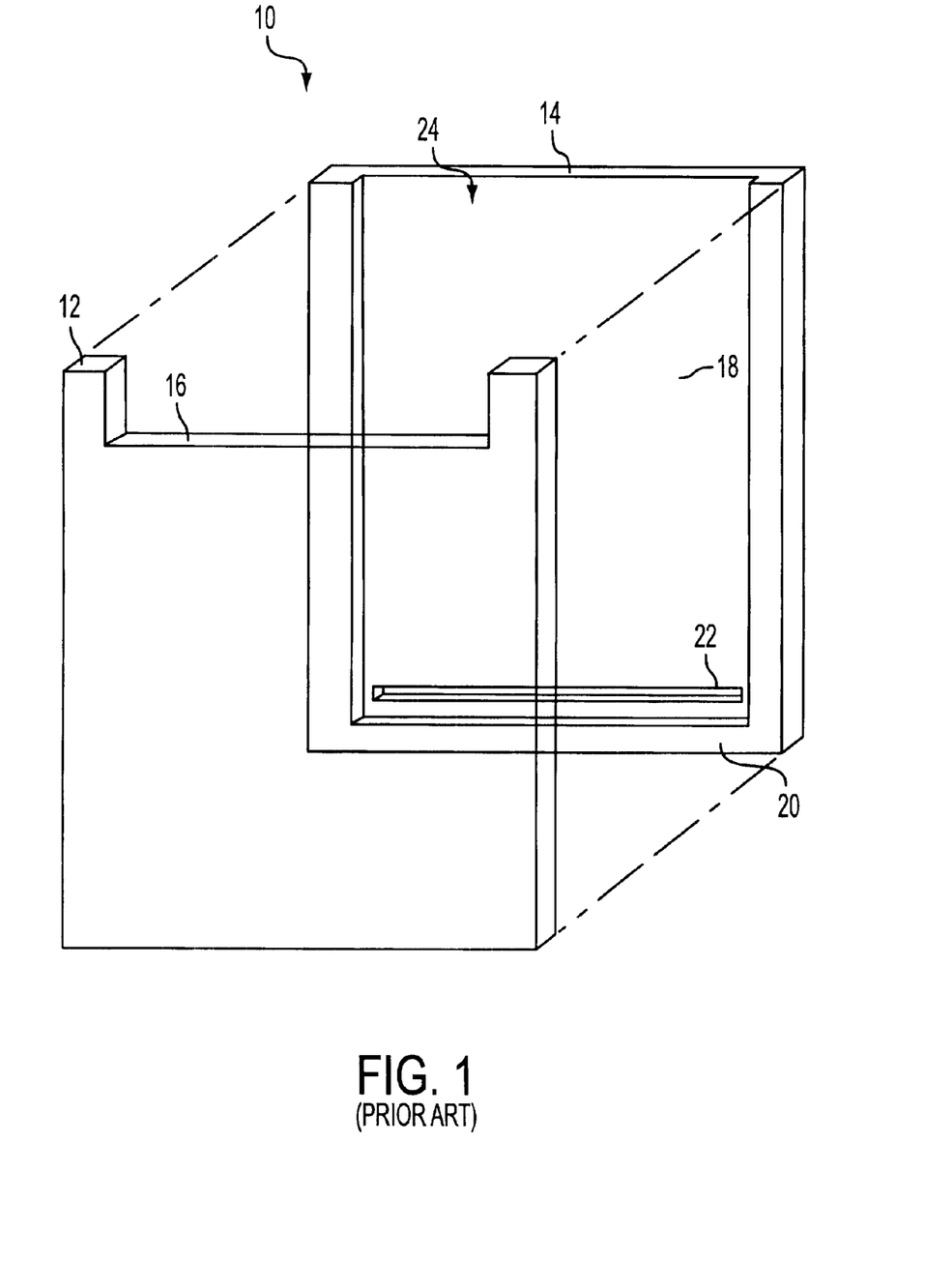
FIG. 1 is a schematic diagram of a previously known gel cassette useful in vertical slab gel electrophoresis.
Figure 2:
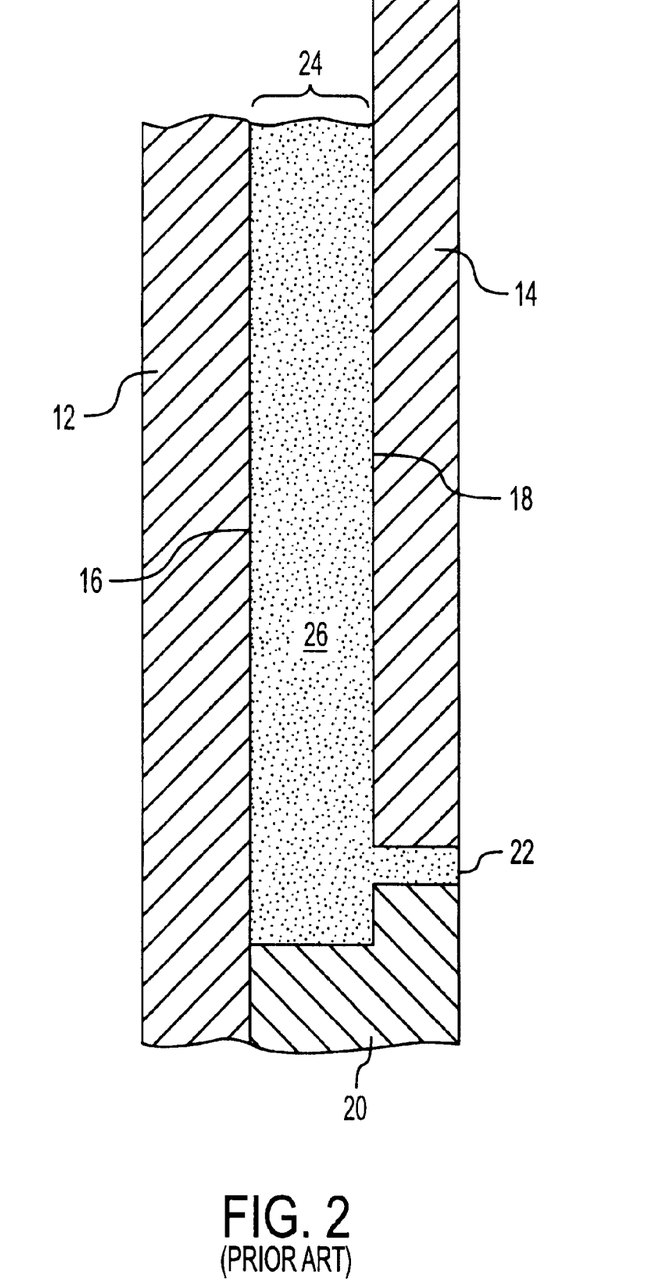
FIG. 2 is a partial cross-sectional view of the gel cassette of FIG. 1.

Referring to FIGS. 1 and 2, a gel cassette used in the prior art for vertical slab gel electrophoresis is described. Such gel cassettes are typically used for polyacrylamide gel electrophoresis, although agarose gels having sufficient structural rigidity can also be run in such vertical devices.

Gel cassette 10 typically comprises two frames (alternatively denominated plates) 12 and 14. Frames 12 and 14 are typically composed of plastic, usually formed by a molding process such as injection molding. Many different plastics are used, such as polyethylene terephthalate, polyvinyl chloride, polymethyl methacrylate, polystyrene, polyethylene, polymethyl polypropylene, cellulose acetates and various of their co-polymers. The plastic typically is transparent so that the progress of the tracking dye through the gel can easily be monitored.

Alternatively, glass plates are used as frames 12 and 14. When glass is used, one or both of the glass plates will often be treated prior to gel polymerization with an agent that adjusts the surface properties of the glass. For example, one or both plates can be treated with a surface agent such as ethyltrimethoxysilane (Dow Chemical, Catalogue No. I-6321) that prevents the subsequently polymerized gel from adhering to the glass; both plates would be so treated if the gel were intended to be removed entirely from the cassette after electrophoresis. Conversely, one of the two glass plates can be treated with an agent that promotes gel adherence, such as γ-methacryloxypropyltrimethoxysilane (Sigma Chemical Company, St. Louis, Mo., Catalog No. M6514), to ensure that the gel remains affixed to one of the two plates when the plates are pulled apart after the electrophoresis is completed.

Frames 12 and 14 have interior surfaces 16 and 18, respectively. Plate 14 further includes U-shaped raised spacer 20. When the two plates are joined, spacer 20 provides the contact of plate 14 with plate 12, thus spacing interior surfaces 16 and 18 at a distance from one another that is fixed by the depth of raised spacer 20. In an alternative often seen when glass plates are used as frames 12 and 14, spacer 20 is provided as a separate member that is nonintegral to plates 12 and 14.

When the two plates are joined, interior surfaces 16 and 18 form a slab-shaped cavity that is sealed by raised spacer 20 except for top opening 24 between plates 12 and 14 and slot 22 at a lower end of plate 14.

During vertical slab gel preparation, slot 22 in plate 14 is reversibly sealed. Gel cassette 10 is held vertical, and a polymerizable liquid gel-forming mixture is poured through top opening 24 into the cavity between plates 12 and 14. The gel-forming liquid polymerizes in situ between plates 12 and 14 and in contact with interior surfaces 16 and 18. Thereafter, the gel cassette is placed into an electrophoresis tank adapted to hold gel cassette 10 vertically, with top and bottom in fluid communication with an anode and cathode.

In order to practice the methods of the present invention with such vertical slab gels, gel label 28 is applied to interior surface 16 or 18 of gel cassette 10, as shown in FIGS. 3 and 4, prior to addition of polymerizable liquid gel-forming mixture.

Positioning label 28 against an interior surface 16 or 18 of gel cassette 10 during polymerization facilitates the maintenance, during subsequent electrophoresis, of a homogeneous electric field, which is desired to assure well-behaved migration of analytes in the gel.

If gel label 28 is provided in sheets or rolls larger than is desired to be contacted to the gel, gel label 28 is first sized for use, as by cutting or tearing along perforations. If indicia 34 are desired to be added to gel label 28—e.g., if gel labels 28 are not pre-printed with such indicia, or if user-specified indicia additional to such preprinted indicia are desired—indicia 34 are added, either before or after sizing of the gel label. Indicia 34 are typically added to a surface of polymeric film 30 lacking coating 32, although indicia 34 can be added to coating 32 when the composition of coating 32 allows. Although addition of indicia 34 is typically performed prior to contact of gel label 28 to interior frame surface 16 or 18, such indicia can be added after gel label 28 is applied to the cassette surface.

Where gel label 28 has a coating 32 on only one side, gel label 28 is applied to interior frame surface 16 or 18 by contact of a surface of polymeric film 30 other than that bearing coating 32, as shown in FIG. 4.

To prevent gel label 28 from becoming dislodged during gel formation, an adhesive layer is usefully bonded to polymeric film 30 at a surface other than that bearing coating 32. Alternatively, and particularly where such adhesive surface is not provided on gel label 28, a small amount of agarose may be applied to the cassette at the desired point of contact, or alternatively to polymeric film 30, and the gel label then applied to the cassette. Alternatively, glycerol, polyvinyl pyrrolidone, carboxymethycellulose, polyethylene glycol, dextran, or any other similar sticky, viscous material may be used to hold polymeric film 30 to cassette 10 during gel formation.

Typically, gel label 28 is placed in contact with interior surface 16 or 18 prior to assembly of gel cassette 10, although label 28 can be placed in contact with surface 16 after cassette assembly by access through slot 22.

Thereafter, the polymerizable liquid gel mixture is added and permitted to polymerize in situ. Upon polymerization, label 28 becomes integral to the gel. If the gel is polyacrylamide and coating 32 contains reactive groups capable of copolymerization therewith—e.g., reactive ethylenically unsaturated groups—gel label 28 becomes covalently bonded to the gel during polymerization.

Horizontal slab gels, typically agarose gels, are usually cast horizontally by solidification in casting trays, a typical example of which is shown in top perspective view in FIG. 5.

Casting tray 50 is typically composed of UV-transparent plastic that is capable of exposure to boiling agarose without fracture, crazing, opacification or deformation. Side walls 52 form two permanent sides of a fluid dam, the bottom of which is provided by surface 54. The two open sides of casting tray 50 are typically reversibly sealed with tape to provide a complete fluid dam during gel solidification.

One more pairs of slots 56 in side walls 52 accommodate removable well-former 58, which is composed of a material that does not significantly adhere to the gel once solidified, permitting removal of well-former 58 after gel solidification.

Figure 6:
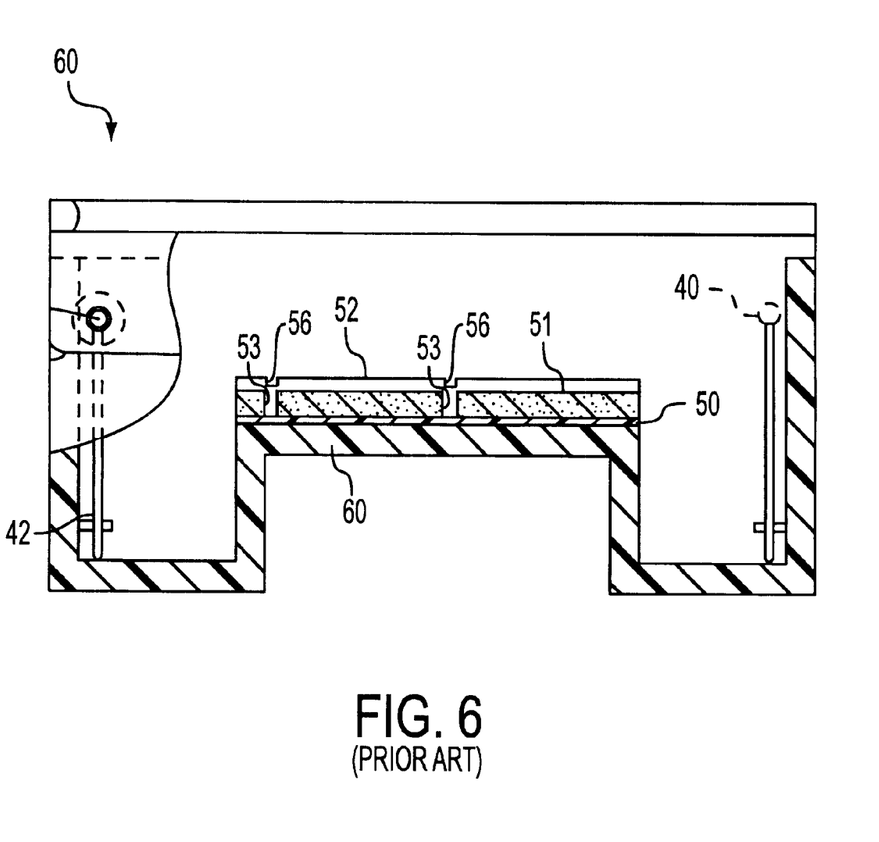
FIG. 6 is a side view of an electrophoresis tank of the prior art that is particularly adapted for horizontal gel electrophoresis of agarose gels.

Typically, agarose is melted in aqueous gel buffer, and the molten agarose poured into casting tray 50 having well-former 58 in place. After the agarose has polymerized, well-former 58 and tape are removed. If of sufficient rigidity, gel 51 can then be placed directly onto support surface 62 of electrophoresis tank 60. Alternatively, and typically, casting tray 50 is placed onto support surface 62 of electrophoresis tank 60, with gel 51 present thereupon, as shown in FIG. 6. Electrophoresis running buffer is placed within the tank to a height sufficient to place gel 51 in fluid communication with anode 42 and cathode 40. Upon application of an electric field, sample 53 migrates through gel 51 toward cathode 40.

Figure 7:
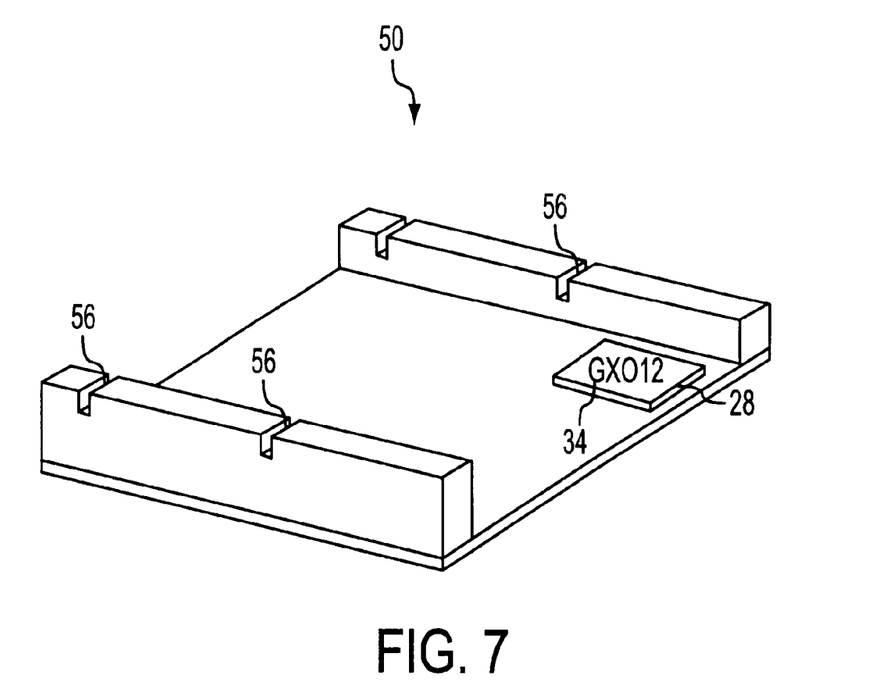
FIG. 7 is a top perspective view of a gel casting tray with a gel label of the present invention positioned for contact with the gel matrix.

In order to practice the methods of the present invention with such horizontal slab gels, gel label 28 is applied to surface 54 of gel casting tray 50 prior to addition of polymerizable liquid gel-forming mixture, typically molten agarose.

Positioning label 28 against an interior surface 16 or 18 of gel cassette 10 during polymerization facilitates the maintenance, during subsequent electrophoresis, of a homogeneous electric field, which is desired to assure well-behaved migration of analytes in the gel.

If gel label 28 is provided in sheets or rolls larger than is desired to be contacted to the gel, gel label 28 is first sized for use, as by cutting or tearing along perforations. If indicia 34 are desired to be added to gel label 28—e.g., if gel labels 28 are not pre-printed with such indicia, or if user-specified indicia additional to such preprinted indicia are desired—indicia 34 are added. Indicia 34 are typically added to a surface of polymeric film 30 lacking coating 32, although indicia 34 can be added to coating 32 when the composition of coating 32 allows. Although addition of indicia 34 is typically performed prior to contact of gel label 28 to casting tray surface 54, such indicia can be added after gel label 28 is applied to the casting tray surface.

Where gel label 28 has a coating 32 on only one side, gel label 28 is applied to casting frame surface 54 by contact of a surface of polymeric film 30 other than that bearing coating 32.

To prevent gel label 28 from becoming dislodged during gel formation, a pressure sensitive reversible adhesive layer is usefully bonded to polymeric film 30 at a surface other than that bearing coating 32. Alternatively, and particularly where such adhesive surface is not provided on gel label 28, a small amount of agarose may be applied to the cassette at the desired point of contact, or alternatively to polymeric film 30, and the gel label then applied to the cassette. Alternatively, glycerol, polyvinyl pyrrolidone, carboxymethycellulose, polyethylene glycol, dextran, or any other similar sticky, viscous material may be used to hold polymeric film 30 to cassette 10 during gel formation.

Thereafter, the polymerizable liquid gel mixture, typically molten agarose, is added and permitted to polymerize in situ. Upon polymerization, label 28 becomes integral to the gel.

All patents, patent publications, and published references cited herein are hereby incorporated by reference in their entirety as if each has been incorporated individually herein.

Persons skilled in the art will recognize that modifications that are equivalent to the above-exemplified methods, articles, and kits may be made without departing from the spirit of the above-exemplified invention. All such equivalent modifications are within the scope of the present invention, which is limited only by the following claims.

We claim:

1. A method of detectably labeling a polymer gel, comprising:
   bonding to said gel, during said gel's polymerization, a polymeric film having indicia that are detectable after said film is so bonded to said gel,
   wherein said polymeric film has a smaller surface area than said gel.
2. The method of claim 1, wherein said gel is a polyacrylamide gel.
3. The method of claim 2, wherein said polyacrylamide gel is a polymerization product of acrylamide monomer crosslinked with N,N'-methylenebisacrylamide.
4. The method of claim 1, wherein said gel is an agarose gel.
5. The method of claim 4, wherein said agarose is a natural agarose.
6. The method of claim 1, wherein said polymeric film consists essentially of a polymer, or is a laminate at least one layer of which consists essentially of a polymer, selected from the group consisting of polyester, Mylas, polymethylpentene, polystyrene, polypropylene, polyethylene, styreneacrylonitrile copolymers, polycarbonate, cellulose acetate proprionate, cellulose acetate butyrate, nitrile-acrylonitrilestyrene copolymers, polyacrylate, polyterephthalate, polymethacrylate, and acrylonitrile-butadiene-styrene copolymer.
7. The method of claim 6, where said polymeric film consists essentially of polyester.
8. The method of claim 1, wherein said polymeric film is substantially transparent to visible light.
9. The method of claim 1, wherein said bonding is covalent.
10. The method of claim 1, wherein said bonding is noncovalent, but of sufficient strength to prevent separation of the polymeric film from the gel during ordinary handling.
11. The method of claim 1, wherein said polymeric film bonds directly to said gel.
12. The method of claim 1, wherein said polymeric film bonds to said gel indirectly through a coating disposed between said polymeric film and said gel.
13. The method of claim 12, wherein said coating consists essentially of a hydrophilic resin.
14. The method of claim 13, wherein said hydrophilic resin has ethylenically unsaturated groups.
15. The method of claim 14, wherein said resin is allylglycidylagarose.
16. The method of claim 14, wherein said resin is allylglycidyldextran.
17. The method of claim 12, wherein said coating consists of successive layers, from polymeric film to gel, of vinyl acetate-maleic acid copolymer and dried agarose.
18. The method of claim 1, wherein said indicia are detectable before electrophoresis.
19. The method of claim 1, wherein said indicia are detectable upon epiillumination.
20. The method of claim 1, wherein said indicia are detectable upon transillumination.
21. The method of claim 1, wherein said indicia are capable of fluorescing.
22. The method of claim 1, wherein said indicia are capable of chemiluminescing.
23. The method of claim 1, wherein said indicia contain ligands that are capable of binding detectable reagents.
24. A polymer gel labeled with detectable indicia, comprising:
   a polymer gel; and
   a polymeric film having detectable indicia, wherein said polymeric film is bonded to said polymer gel, said indicia are detectable with the film so bonded, and said polymeric film has a smaller surface area than said gel.
25. The labeled polymer gel of claim 24, wherein said gel is a polyacrylamide gel.
26. The labeled polymer gel of claim 25, wherein said polyacrylamide is a polymerization product of acrylamide monomer crosslinked with N,N'-methylenebisacrylamide.
27. The labeled polymer gel of claim 24, wherein said gel is an agarose gel.
28. The labeled polymer gel of claim 27, wherein said agarose is a natural agarose.
29. The labeled polymer gel of claim 24, wherein said polymeric film consists essentially of a polymer, or is a laminate at least one layer of which consists essentially of a polymer, selected from the group consisting of polyester, mylar, polymethylpentene, polystyrene, polypropylene, polyethylene, styreneacrylonitrile copolymers, polycarbonate, cellulose acetate proprionate, cellulose acetate butyrate, nitrile-acrylonitrilestyrene copolymers, polyacrylate, polyterephthalate, polymethacrylate, and acrylonitrile-butadiene-styrene copolymer.
30. The labeled polymer gel of claim 29, where said polymeric film consists essentially of polyester.
31. The labeled polymer gel of claim 24, wherein said polymeric film is substantially transparent to visible light.
32. The labeled polymer gel of claim 24, wherein said polymeric film is covalently bonded to said polymer gel.
33. The labeled polymer gel of claim 24, wherein said polymeric film is bonded noncovalently, but sufficiently strongly to said polymer gel so as to prevent separation of the polymeric film from the gel during ordinary handling.
34. The labeled polymer gel of claim 24, wherein said polymeric film is bonded directly to said gel.
35. The labeled polymer gel of claim 24, wherein said polymeric film is bonded to said gel indirectly through a coating disposed between said polymeric film and said gel.
36. The labeled polymer gel of claim 35, wherein said coating consists essentially of a hydrophilic resin.
37. The labeled polymer gel of claim 36, wherein said hydrophilic resin has ethylenically unsaturated groups.
38. The labeled polymer gel of claim 37, wherein said resin is allylglycidylagarose.
39. The labeled polymer gel of claim 37, wherein said resin is allylglycidyldextran.

40. The labeled polymer gel of claim 35, wherein said coating consists of successive layers, from polymeric film to gel, of vinyl acetate-maleic acid copolymer and dried agarose.

41. The labeled polymer gel of claim 24, wherein said indicia are detectable before electrophoresis.

42. The labeled polymer gel of claim 24, wherein said indicia are detectable upon epiillumination.

43. The labeled polymer gel of claim 24, wherein said indicia are detectable upon transillumination.

44. The labeled polymer gel of claim 24, wherein said indicia are capable of fluorescing.

45. The labeled polymer gel of claim 24, wherein said indicia are capable of chemiluminescing.

46. The labeled polymer gel of claim 24, wherein said indicia contain ligands that are capable of binding detectable reagents.

* * * * *